(12) United States Patent
Scalf et al.

(10) Patent No.: US 10,480,503 B2
(45) Date of Patent: Nov. 19, 2019

(54) PORTABLE FOODSTUFF CONTAINER

(71) Applicant: Midea Group Co., Ltd., Beijiao, Shunde, Foshan (CN)

(72) Inventors: Eric Scalf, Louisville, KY (US);
Robert M. Digman, Goshen, KY (US);
Paul Staun, Louisville, KY (US)

(73) Assignee: MIDEA GROUP CO., LTD., Beijiao, Shunde, Foshan, Guangdong (CN)

( * ) Notice: Subject to any disclaimer, the term of this patent is extended or adjusted under 35 U.S.C. 154(b) by 0 days.

(21) Appl. No.: 15/721,104

(22) Filed: Sep. 29, 2017

(65) Prior Publication Data
US 2019/0101112 A1 Apr. 4, 2019

(51) Int. Cl.
| | |
|---|---|
| *F04B 49/06* | (2006.01) |
| *A47J 47/01* | (2006.01) |
| *G01C 19/00* | (2013.01) |
| *G01F 23/20* | (2006.01) |
| *G01F 23/296* | (2006.01) |
| *G01N 11/02* | (2006.01) |

(Continued)

(52) U.S. Cl.
CPC ............. *F04B 49/06* (2013.01); *A47J 47/01* (2013.01); *F04B 13/00* (2013.01); *G01C 19/00* (2013.01); *G01F 13/00* (2013.01); *G01F 13/006* (2013.01); *G01F 23/20* (2013.01); *G01F 23/296* (2013.01); *G01F 23/2962* (2013.01); *G01N 11/02* (2013.01); *A47J 2203/00* (2013.01); *F04B 17/03* (2013.01); *F04B 23/028* (2013.01); *F04B 51/00* (2013.01)

(58) Field of Classification Search
CPC ........ F04B 49/06; F04B 51/00; F04B 23/028; F04B 17/03; G01F 23/296; G01F 23/20; G01C 19/00; A47J 47/01; A47J 2203/00; G01N 11/02

USPC .................................................... 222/52, 63
See application file for complete search history.

(56) References Cited

U.S. PATENT DOCUMENTS

| | | |
|---|---|---|
| 3,178,061 A | 4/1965 | Giacalone et al. |
| 5,884,808 A | 3/1999 | Muderlak et al. |

(Continued)

FOREIGN PATENT DOCUMENTS

| | | | |
|---|---|---|---|
| CN | 102166104 A | * | 8/2011 |
| CN | 102166104 A | | 8/2011 |

(Continued)

OTHER PUBLICATIONS

International Search Report and Written Opinion issued in Application No. PCT/CN2018/074269 dated Jul. 4, 2018.

(Continued)

*Primary Examiner* — Donnell A Long
(74) *Attorney, Agent, or Firm* — Middleton Reutlinger

(57) ABSTRACT

A portable foodstuff container and method of dispensing foodstuff from the portable container are disclosed herein. Such a portable foodstuff may include a portable body with a reservoir configured to contain a foodstuff and a dispenser configured to dispense the foodstuff contained in the reservoir, a pump disposed within the body and configured to convey the foodstuff from the reservoir to the dispenser when activated to dispense the foodstuff through the dispenser, and a controller disposed in the body and coupled to the pump. The controller may be configured to activate the pump to dispense a user-selected amount of foodstuff from the dispenser.

27 Claims, 10 Drawing Sheets

(51) Int. Cl.
*G01F 13/00* (2006.01)
*F04B 13/00* (2006.01)
*F04B 17/03* (2006.01)
*F04B 23/02* (2006.01)
*F04B 51/00* (2006.01)

(56) References Cited

U.S. PATENT DOCUMENTS

| | | | |
|---|---|---|---|
| 6,036,055 A | 3/2000 | Mogadam et al. | |
| 6,422,421 B1* | 7/2002 | Freudinger | B67D 1/0005 222/529 |
| 6,504,481 B2 | 1/2003 | Teller | |
| 6,652,481 B1* | 11/2003 | Brown | A61J 19/00 600/573 |
| 7,690,540 B1* | 4/2010 | Owens | G05D 7/0676 222/175 |
| 8,608,026 B1 | 12/2013 | Temko et al. | |
| 8,655,732 B1 | 2/2014 | Wilinski et al. | |
| 8,899,450 B2 | 12/2014 | Johansson et al. | |
| 8,905,330 B2 | 12/2014 | Paukovits et al. | |
| 9,022,257 B2 | 5/2015 | Keating et al. | |
| 9,247,719 B1 | 2/2016 | Bennett et al. | |
| 9,557,097 B2 | 1/2017 | McMahan et al. | |
| 2006/0097003 A1 | 5/2006 | Emmendoerfer et al. | |
| 2008/0054015 A1 | 3/2008 | Moezidis | |
| 2008/0195251 A1 | 8/2008 | Milner | |
| 2011/0265562 A1 | 11/2011 | Li | |
| 2013/0105512 A1* | 5/2013 | McGill | A23G 9/045 222/39 |
| 2014/0008383 A1* | 1/2014 | Mergener | F16N 3/12 222/1 |
| 2014/0138402 A1* | 5/2014 | Warren | A47K 5/1202 222/2 |
| 2015/0069082 A1 | 3/2015 | Breeden | |
| 2015/0182797 A1 | 7/2015 | Wernow et al. | |
| 2015/0337588 A1 | 11/2015 | Kanhai | |
| 2016/0025545 A1* | 1/2016 | Saltzgiver | G01F 23/263 73/304 C |
| 2016/0159632 A1 | 6/2016 | Wheatley et al. | |
| 2016/0159633 A1 | 6/2016 | Diffenderfer | |
| 2017/0029263 A1* | 2/2017 | Mag | B67D 3/003 |
| 2017/0121167 A1* | 5/2017 | Johnson | A47J 31/46 |
| 2017/0340147 A1* | 11/2017 | Hambrock | A47G 19/2227 |
| 2018/0099068 A1* | 4/2018 | Pitcher | A61L 9/14 |

FOREIGN PATENT DOCUMENTS

| | | |
|---|---|---|
| CN | 202191210 U | 4/2012 |
| CN | 104223994 A | 12/2014 |
| CN | 105455699 A | 4/2016 |
| CN | 106573164 A | 4/2017 |
| WO | 2016145027 A1 | 9/2016 |
| WO | 2017075298 A1 | 5/2017 |

OTHER PUBLICATIONS

Bonnington, Christina, Alcohol Dispenser, Jan. 5, 2016.
Vremi Olive Oil Dispenser Bottle—17 Oz Oil Bottle Glass with No Drip Bottle Spout—Oil Pourer Dispensing Bottles for Kitchen—Olive Oil Glass Dispenser to Measure Cooking Vegetable Oil and Vinegar, May 23, 2017, https://www.amazon.com/Vremi-Olive-Oil-Dispenser-Bottle/dp/B0171XUC2W/ref=zg_bs . . . .
ScivoKaval Oil Dispenser with Press and Measure Non Spill Spout 17 Ounce Vinegar Dispenser Glass Bottle, May 23, 2017, www.amazon.com/ScivoKaval-Dispenser-Measure-Vinegar-Bottle/dp/B01M2WRL . . . .
Chewy.com: Petnet SmartFeeder Automatic Pet Feeder, May 23, 2017, www.chewy.com.
Dash: In-Store Spice Dispensing Machine, Feb. 8, 2016.
Vat19: Sugar Please Automatic Sugar Dispenser; httpVat19s://www.vat19.com/item/sugar-please-automatic-sugar-dispenser, Jul. 19, 2014.
Amazon: Made 1.0-Quart Round Food Storage and Measuring Container: https://www.amazon.com/1-0-Quart-Round-Storage-Measuring-Container/dp/B010FWFSJK?th=1 (spices).
Pantrychic Store & Dispense System: http://www.pantrychic.com/product-overview/; Mar. 28, 2015.

\* cited by examiner

PORTABLE FOODSTUFF CONTAINER

BACKGROUND

Conventionally, measuring of foodstuffs such as liquids or dry ingredients for use in cooking requires the use of a measuring device (e.g. a measuring cup, measuring spoon, or the like) to manually measure a desired amount of a foodstuff. A measuring cup typically includes lines at different levels corresponding to different amounts, while measuring spoons are generally provided in different sizes to accommodate different amounts. When following a recipe during cooking, different foodstuffs are generally measured in various measuring devices and then placed into a secondary container for mixing, cooking, or the like, which creates additional mess, items to clean, etc. In addition, manual measurement can be inaccurate, particularly when a cook is busy trying to manage multiple tasks at once. In certain instances, it may be desirable to minimize the number of items utilized for measurement of foodstuffs, which in turn also minimizes the number of items that require cleaning. A need therefore exists in the art for simplifying the measurement process during cooking, as well as reducing the burden on users (e.g., cooks or chefs).

SUMMARY

The invention addresses these and other problems associated with the art by providing a portable foodstuff container and method of dispensing from a foodstuff from the portable container that dispense controlled amounts of foodstuffs stored in the portable container.

Therefore, consistent with one aspect of the invention, a portable foodstuff container may include a portable body including a reservoir configured to contain a foodstuff and a dispenser configured to dispense the foodstuff contained in the reservoir, a pump disposed within the body and configured to convey the foodstuff from the reservoir to the dispenser when activated to dispense the foodstuff through the dispenser, and a controller disposed in the body and coupled to the pump, where the controller is configured to activate the pump to dispense a user-selected amount of foodstuff from the dispenser.

In some embodiments the container further includes a flow meter disposed in the body and configured to measure an amount of foodstuff conveyed by the pump, and the controller is configured to deactivate the pump upon sensing with the flow meter that the user-selected amount has been dispensed. Moreover, in some embodiments, the controller is configured to determine an amount of foodstuff present in the reservoir based on one or more readings from the flow meter.

In addition, some embodiments may further include a user interface disposed on the body and coupled to the controller to receive user input selecting the user-selected amount, and where the user interface includes a control that a user selects to dispense the user-selected amount of foodstuff. Some embodiments may also include a dial disposed on the body and coupled to the controller to receive user input selecting the user-selected amount by rotation. Some embodiments may further include a control disposed on the body and coupled to the controller to change a unit of measure of the user-selected amount. Some embodiments may also include a display disposed on the body and coupled to the controller to transmit and/or receive information to and from a user.

Some embodiments may further include a level sensor in the body and coupled to the controller to sense an amount of the foodstuff remaining in the reservoir. In addition, some embodiments may also include a control disposed on the body and coupled to the controller to start and/or stop dispensing the foodstuff. In addition, some embodiments may further include a battery in the body configured to provide power to the pump and the controller. In addition, in some embodiments, the battery is rechargeable.

Moreover, in some embodiments, the pump is disposed in a channel between the reservoir and the dispenser. In some embodiments, the dispenser is located proximate a bottom portion of the body. Further, in some embodiments, the dispenser is located proximate a top portion of the body.

In some embodiments, the body further includes a gyroscope, where the controller is coupled to the gyroscope. Moreover, in some embodiments, the controller is further configured to disable the pump when the gyroscope senses that the body is not in a dispensing orientation. Further, in some embodiments, the controller is further configured to disable the pump when the gyroscope senses that the body is in a dispensing orientation but there is an absence of user input. In some embodiments, the controller is further configured to activate the pump when the gyroscope senses that the body is in a dispensing orientation and the user-selected amount has been received from a user.

Also, in some embodiments, the controller is configured to communicate with a mobile computing device to receive the user-selected amount. In some embodiments, the mobile computing device further includes an application configured to accept user input of the user-selected amount and communicate the user-selected amount to the controller. Moreover, in some embodiments, the controller is further configured to activate the pump to free flow based on user input. In addition, in some embodiments, the foodstuff is a liquid, while in some embodiments, the foodstuff is a dry ingredient. In some embodiments, the controller is further configured to activate the pump in response to tilting of the body. In some embodiments, the container is configured for storage in a refrigerator and includes a battery charging circuit configured to charge a battery of the container when the container is stored in the refrigerator. In addition, in some embodiments, the controller is further configured to activate the pump when the gyroscope senses that the body is in a dispensing orientation and a user control is selected.

Consistent with another aspect of the invention, a portable foodstuff container may include a portable body including a reservoir configured to contain a foodstuff and a dispenser configured to selectively dispense the foodstuff contained in the reservoir, a flow meter disposed in the body and configured to measure an amount of foodstuff dispensed by the dispenser, and a controller coupled to the flow meter and the dispenser, where the controller is configured to control the dispenser to dispense a user-selected amount of foodstuff in response to the amount of foodstuff sensed by the flow meter.

In addition, some embodiments may also include a user interface disposed on the body and coupled to the controller to receive user input selecting the user-selected input, and where the user interface includes a control that a user selects to dispense the user-selected amount of foodstuff. In addition, some embodiments may further include a dial disposed on the body and coupled to the controller to receive user input selecting the user-selected amount by rotation. Some embodiments may also include a control disposed on the body and coupled to the controller to change a unit of measure of the user-selected amount. In addition, some embodiments may further include a display disposed on the body and coupled to the controller to transmit to and/or receive information from a user.

Some embodiments may also include a level sensor in the body and coupled to the controller to sense an amount of the foodstuff remaining in the reservoir. In addition, some embodiments may further include a control disposed on the body and coupled to the controller to start and/or stop dispensing the foodstuff. In addition, some embodiments may further include a battery in the body configured to provide power to the controller. Moreover, in some embodiments, the battery is rechargeable.

Moreover, in some embodiments, the flow meter is disposed in a channel between the reservoir and the dispenser. Moreover, in some embodiments, the dispenser is located proximate a bottom portion of the body, while in some embodiments, the dispenser is located proximate a top portion of the body. In addition, in some embodiments the body further includes a gyroscope, where the controller is coupled to the gyroscope. Further, in some embodiments, the controller is further configured to deactivate the dispenser when the gyroscope senses that the body is not in a dispensing orientation. In some embodiments, the controller is further configured to deactivate the dispenser when the gyroscope senses that the body is in a dispensing orientation but there is an absence of user input. In addition, in some embodiments, the controller is further configured to activate the dispenser when the gyroscope senses that the body is in a dispensing orientation and the user-selected amount has been received from a user.

Moreover, in some embodiments, the controller is configured to communicate with a mobile computing device to receive the user-selected amount. In some embodiments, the mobile computing device further includes an application configured to accept user input of the user-selected amount and communicate the user-selected amount to the controller. Moreover, in some embodiments, the foodstuff is a liquid, while in some embodiments, the foodstuff is a dry ingredient. Moreover, in some embodiments, the controller is further configured to activate the pump when the gyroscope senses that the body is in a dispensing orientation and a control is selected. Further, in some embodiments, the container is configured for storage in a refrigerator and includes a battery charging circuit configured to charge a battery of the container when the container is stored in the refrigerator.

Consistent with another aspect of the invention, a method of dispensing a portable foodstuff from a container may be provided. The container may include a portable body including a reservoir configured to contain a foodstuff and a dispenser configured to dispense the foodstuff contained in the reservoir, and the method may include receiving, by a controller, a user-selected amount of the foodstuff to be dispensed, and dispensing, based on a signal from the controller, the user-selected amount of the foodstuff out of the reservoir by activating a pump.

Some embodiments may also include receiving, by the controller, an indication of an orientation of the body by a gyroscope, where dispensing the user-selected amount of the foodstuff is performed in response to determining from the gyroscope that the body is in a dispensing orientation. In addition, some embodiments may further include communicating an amount of the foodstuff remaining in the reservoir to a mobile computing device. In addition, in some embodiments, the controller is in communication with a mobile computing device configured to receive user input selecting the user-selected amount of foodstuff and communicate the user-selected amount of foodstuff to the controller.

Some embodiments may also include receiving, by the controller, an amount of foodstuff added to the reservoir, tracking an amount of foodstuff currently in the reservoir based upon the received amount of foodstuff added to the reservoir and an amount of foodstuff dispensed from the reservoir during one or more dispense cycles, and notifying a user when the amount of foodstuff currently in the reservoir is running low.

Consistent with another aspect of the invention, a method of dispensing a foodstuff from a container may be provided. The container may include a portable body including a reservoir configured to contain a foodstuff and a dispenser configured to dispense the foodstuff contained in the reservoir, and the method may include receiving, by a controller, a user-selected amount of the foodstuff to be dispensed, activating the dispenser, based on a signal from the controller, to dispense the foodstuff out of the reservoir through the dispenser, measuring, by a flow meter, an amount of foodstuff dispensed through the dispenser, and deactivating the dispenser when the measured amount of foodstuff matches the user-selected amount of foodstuff to be dispensed.

Some embodiments may also include receiving, by the controller, an indication of an orientation of the body by a gyroscope, where activating the dispenser is performed in response to determining from the gyroscope that the body is in a dispensing orientation. In addition, some embodiments may further include communicating an amount of the foodstuff remaining in the reservoir to a mobile computing device. Moreover, in some embodiments, the controller is in communication with a mobile computing device configured to receive user input selecting the user-selected amount of foodstuff and communicate the user-selected amount of foodstuff to the controller.

In addition, some embodiments may also include receiving, by the controller, an amount of foodstuff added to the reservoir, tracking an amount of foodstuff currently in the reservoir based upon the received amount of foodstuff added to the reservoir and an amount of foodstuff dispensed from the reservoir during one or more dispense cycles, and notifying a user when the amount of foodstuff currently in the reservoir is running low.

Consistent with another aspect of the invention, a method of dispensing a material from a portable container may include sensing tilting of the portable container with a gyroscope coupled to the container, sensing a level change of the material in the portable container during tilting of the portable container with a level sensor, determining a value representative of a viscosity of the material based upon the sensed tilting and sensed level change, and controlling an amount of material dispensed from the portable container using the determined value.

In some embodiments, sensing the level change includes sensing a rate of change in level when the portable container is tilted. Moreover, in some embodiments, controlling the amount of material dispensed from the portable container includes determining a dispense time or a dispense rate of a dispenser of the portable container to dispense a predetermined amount of material from the portable container using the determined value. In some embodiments, determining the dispense time or dispense rate of the dispenser includes determining an unscaled dispense time or dispense rate corresponding to the predetermined amount of material at a baseline viscosity, and scaling the unscaled dispense time or dispense rate using the determined value.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described example embodiments of the invention. This summary is merely provided to introduce a selection of concepts that are further described below in the detailed description, and is not intended to identify key or essential features of the claimed subject matter, nor is it intended to be used as an aid in limiting the scope of the claimed subject matter.

DETAILED DESCRIPTION

Embodiments consistent with the invention may be used to dispense controlled amounts of a foodstuff from a portable container. In particular, in some embodiments consistent with the invention, a portable foodstuff container may include, in part: a portable body that includes a reservoir that contains the foodstuff and a dispenser for dispensing the foodstuff from the reservoir, a pump within the body and configured to convey the foodstuff from the reservoir to the dispenser when activated to dispense the foodstuff through the dispenser, and a controller disposed in the body, coupled to the pump, and configured to activate the pump to dispense an amount of foodstuff selected by a user from the dispenser. In other embodiments consistent with the invention, a portable foodstuff container may include, at least in part: a portable body that includes a reservoir that contains the foodstuff and a dispenser for selectively dispensing the foodstuff from the reservoir, a flow meter disposed in the body that may be configured to measure an amount of foodstuff dispensed by the dispenser, and a controller coupled to the flow meter and the dispenser and configured to control the disperser so that the dispenser dispenses a user-selected amount of foodstuff in response to the amount of foodstuff sensed by the flow meter.

Numerous variations and modifications will be apparent to one of ordinary skill in the art, as will become apparent from the description below. Therefore, the invention is not limited to the specific implementations discussed herein.

Figure 1:
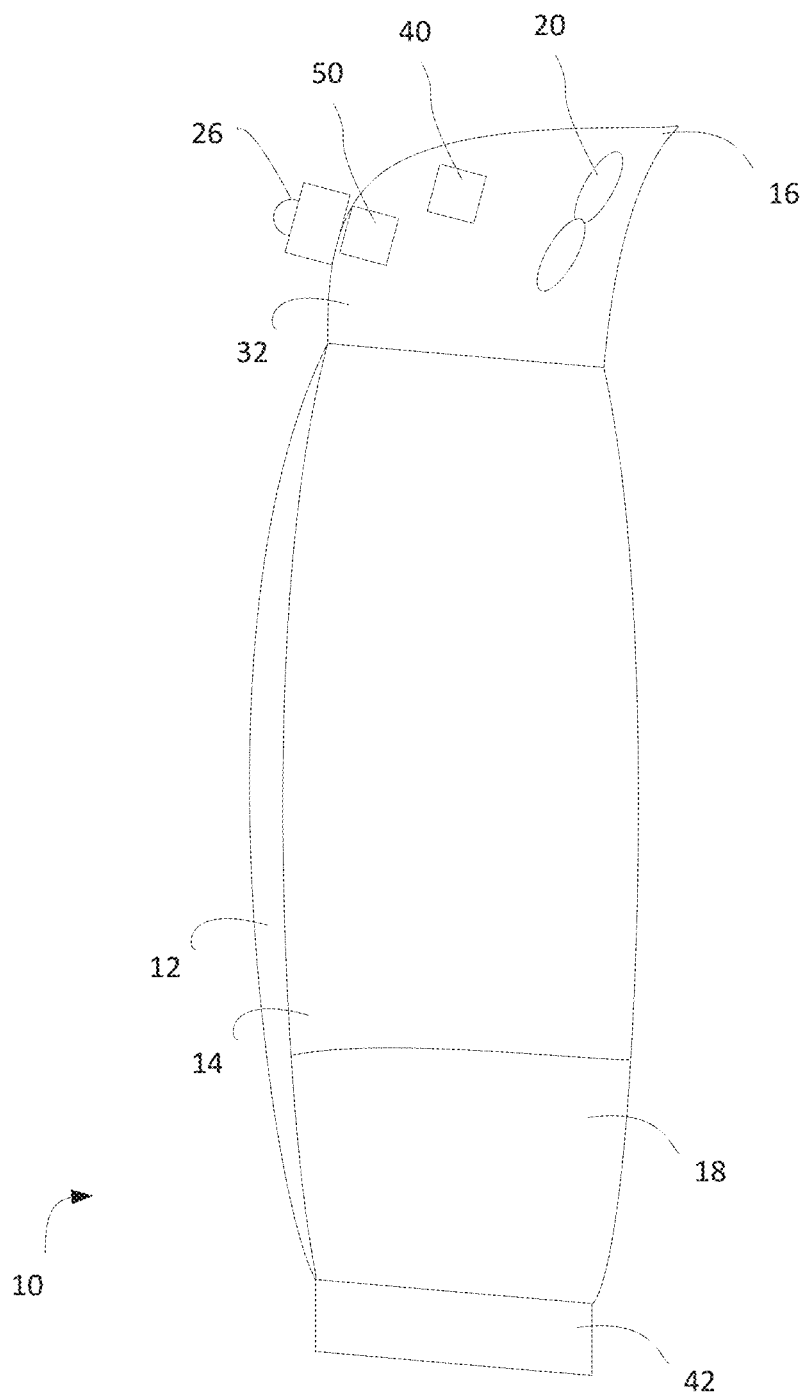
FIG. 1 is a functional vertical section of a portable foodstuff container consistent with some embodiments of the invention.
Figure 2:
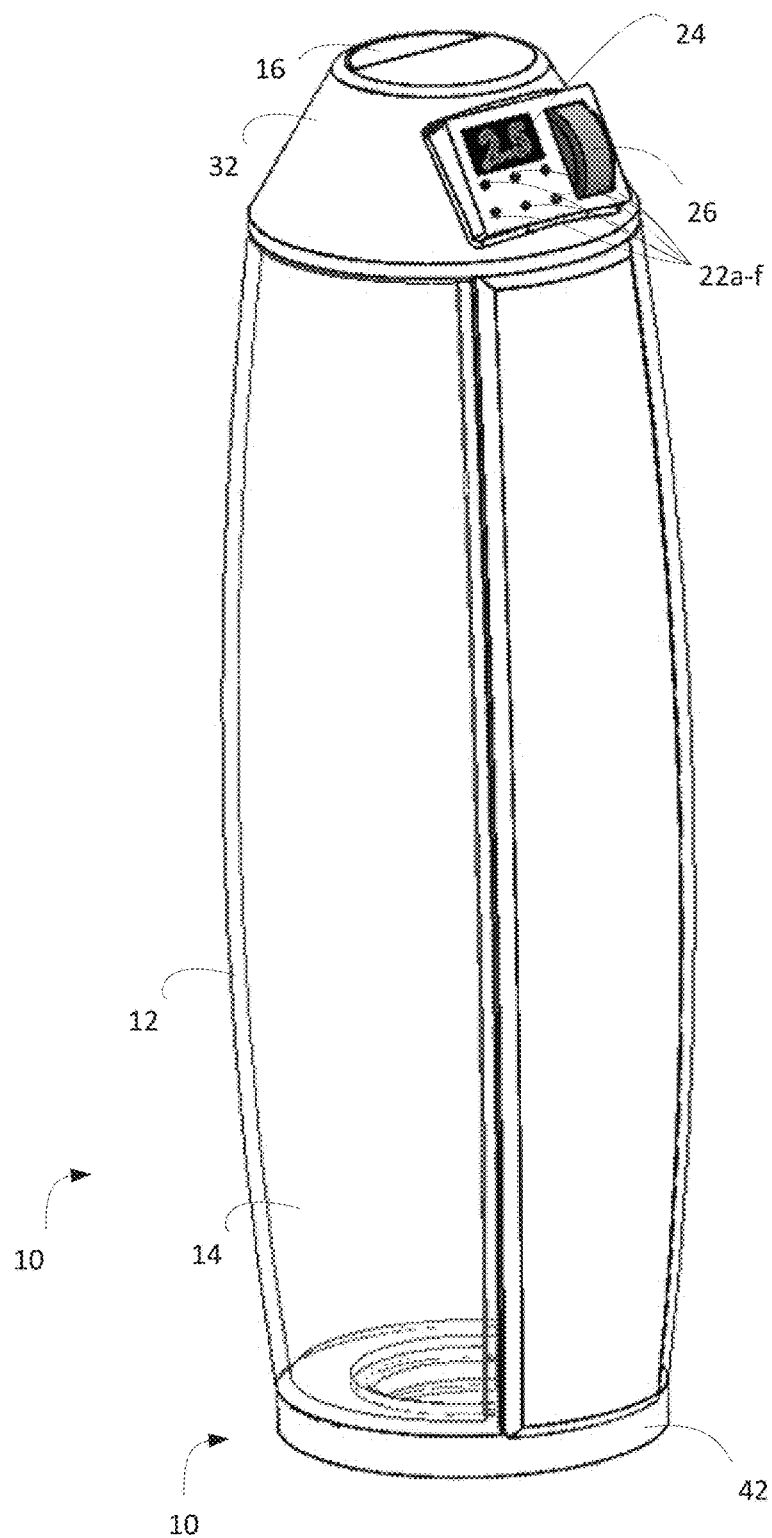
FIG. 2 is a perspective view of a portable foodstuff container consistent with some embodiments of the invention.
Figure 3:
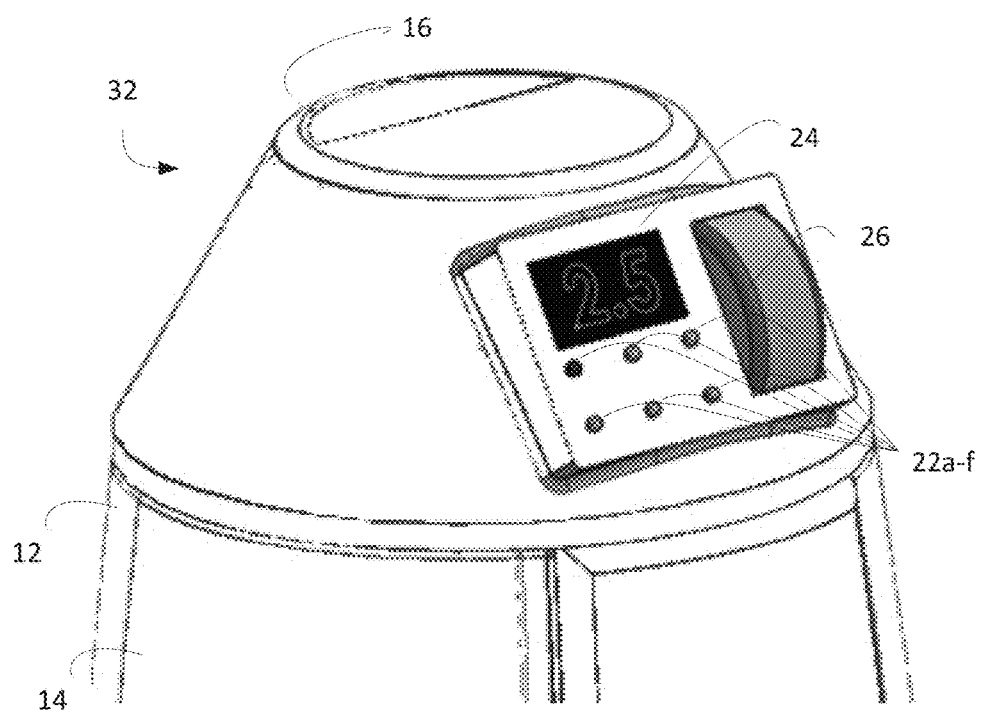
FIG. 3 is a perspective view of a top portion of the portable foodstuff container of FIG. 2.
Figure 4:
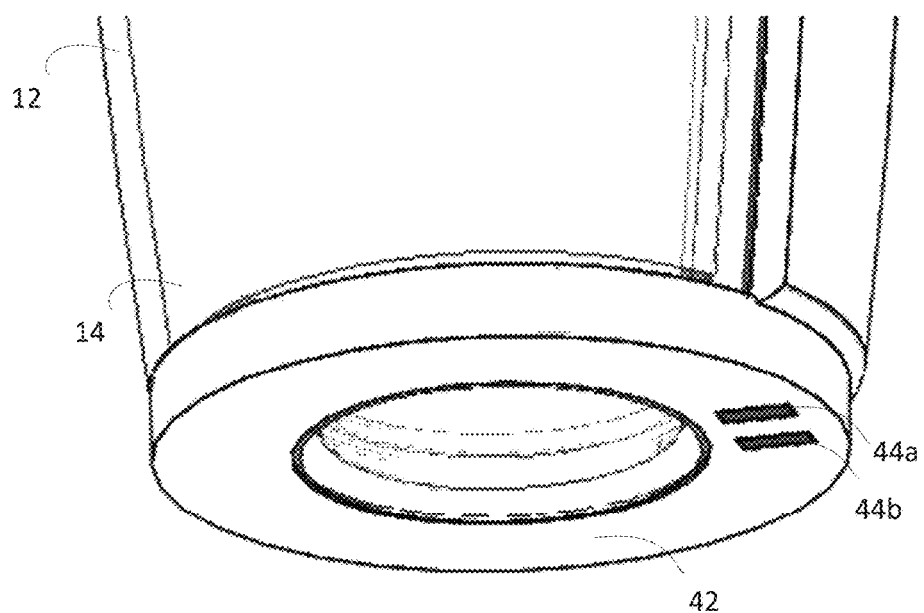
FIG. 4 is a perspective view of a bottom portion of the portable foodstuff container of FIG. 2.

Turning now to the drawings, wherein like numbers denote like parts throughout the several views, FIG. 1 illustrates an example portable foodstuff container 10 in which various technologies and techniques may be described herein may be implemented. Such a portable foodstuff container 10 may be sized and configured for carrying by a user, and may in some instances be sized and configured as a handheld container, and may include a handle and/or grippable surface to facilitate use and movement of the container throughout a kitchen by a user. In addition, it is typically desirable for the container to be internally powered such that no power cord is needed for operation. Portable foodstuff container 10 may include a portable body 12, which may further contain a reservoir 14 and a dispenser 16. In some embodiments, the portable body 12 may be tall and cylindrically shaped, as illustrated in FIG. 1, but this is not to be understood as limiting. The size and shape of the container 10 and/or the portable body 12 may vary widely based on the type of foodstuff 18 contained therein; more particularly, the size of the container 10 and/or the portable body 12 may vary based on the amount of the foodstuff 18 container therein that may be typically utilized when cooking. The foodstuff 18 within the reservoir 14 may be any ingredient desired for cooking, including both liquid ingredients and dry ingredients. For example, if the foodstuff is a rare spice, rare sauce or rare oil, which may be utilized infrequently and in small amounts, the container 10 and/or portable body 12 may be much smaller than if the foodstuff were olive oil, which may be utilized more frequently and in larger amounts. In some embodiments, the reservoir 14 may be constructed of a transparent or semi-transparent material, so that the foodstuff 18 may be seen through the reservoir 14. This may be desirable in order to be able to easily and quickly visualize how much of the foodstuff 18 remains.

Dispenser 16 and reservoir 14 may be integrally formed with one another in some embodiments, while in other embodiments reservoir may be separable from dispenser 16, e.g., through a threaded coupling, a snap fit coupling, etc. Separating dispenser 16 and reservoir 14 may provide access to fill reservoir 14 with foodstuff, or a separate closeable opening may be provided for this purpose. In addition, by separating dispenser 16 and reservoir 14 in some embodiments, dispenser 16 may be usable with multiple reservoirs, e.g., so that one dispenser can be used to dispense a variety of foodstuffs stored in various reservoirs simply by coupling the dispenser to the different reservoirs.

In some in embodiments, the dispenser 16 may be in the form of a pour spout (as illustrated in FIG. 1). In other embodiments, the dispenser 16 may be a manually and/or automatically closable opening through which the foodstuff 18 may pass. Furthermore, the dispenser 16 may utilize various valves to close the dispenser and/or seal the reservoir 14, or alternatively if the pump 20 sufficiently closes the dispenser 16 and/or seals the reservoir, the pump 20 may be used without a separate valve or closure in the dispenser. However, this is not intended to be limiting, as any type of dispenser recognized in the art may be utilized.

In some embodiments, the portable foodstuff container 10 may further contain a pump 20. The pump 20 may be disposed within the body 12, and in some embodiments, the pump 20 may be disposed in a channel between the reservoir 14 and the dispenser 16, although other locations, e.g., in base 42, in a lid, etc., may be used. When the pump 20 is activated, the pump 20 may convey the foodstuff 18 from the reservoir 14 to the dispenser 16, and dispense the foodstuff 18 out of the portable foodstuff container 10 through the dispenser 16.

Figure 7:
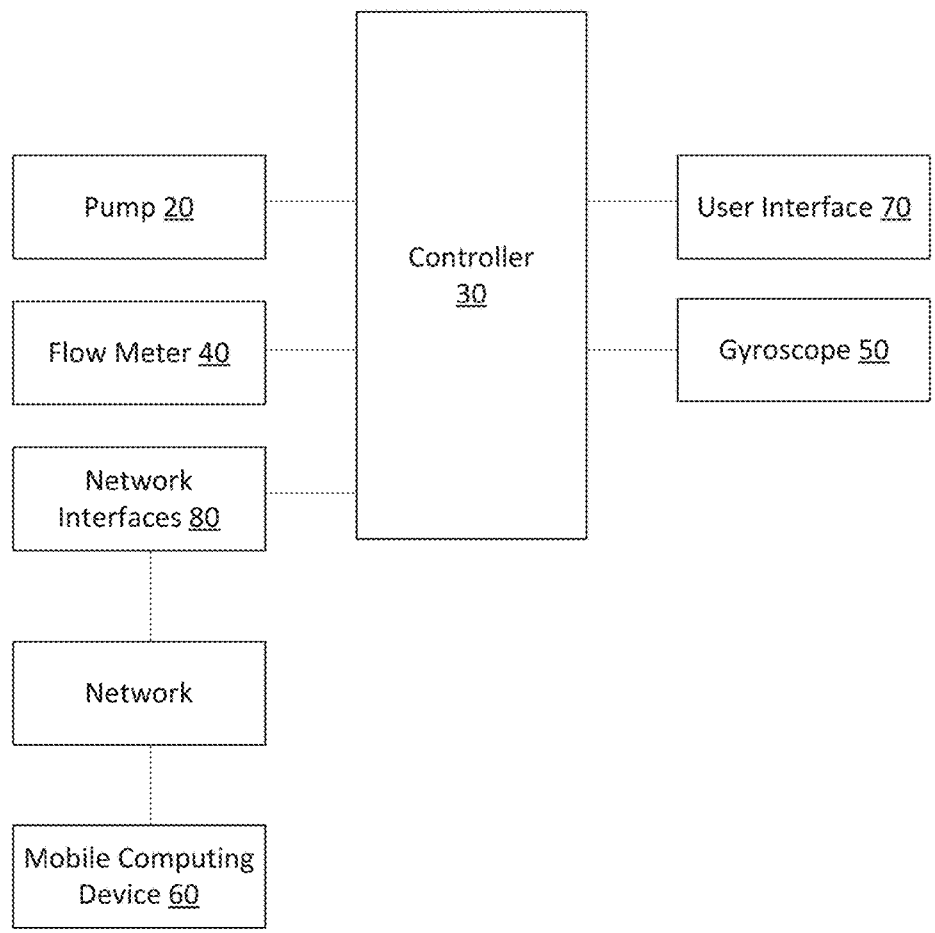
FIG. 7 is a block diagram of an example control system for the portable foodstuff container of FIG. 1.

Turning now to FIG. 7, the portable foodstuff container 10 may be under the control of a controller 30 as a part of the body 12 or top portion 32 that may be coupled to the pump 20. The controller 30 may activate the pump 20 to dispense a user-selected amount of the foodstuff 18 from the dispenser 14. Controller 30 may, for example, include one or more processors and a memory (not shown) within which may be stored program code for execution by the one or more processors. The memory may be embedded in controller 30, but may also be considered to include volatile and/or non-volatile memories, cache memories, flash memories, programmable read-only memories, read-only memories, etc., as well as memory storage physically located elsewhere from controller 30, e.g., in a mass storage device or on a remote computer interfaced with controller 30.

As shown in FIG. 7, the controller 30 may be interfaced with various components, such as one or more user interfaces 70, including various input/output devices such as knobs, dials, sliders, switches, buttons, lights, textual and/or graphics displays, touch screen displays, speakers, image capture devices, microphones, and the like for receiving input from and communicating with a user. Specifically, the user interface may include one or more dials 26, buttons 22a-f, and/or displays 24. The controller 30 may also be interfaced with one or more additional components such as, a level sensor, weight sensor, thermocouples within the body 12, a gyroscope 50 within the body 12 or top portion 32, and so on. In some embodiments, controller 30 may also be coupled to one or more network interfaces 80, e.g., for interfacing with external devices via wired and/or wireless networks such as Ethernet, Bluetooth, NFC, cellular and other suitable networks. Additional components may also be interfaced with controller 30, as will be appreciated by those of ordinary skill having the benefit of the instant disclosure. Moreover, in some embodiments, at least a portion of controller 30 may be implemented externally from a portable foodstuff container 10, e.g., within a mobile device, a cloud computing environment, etc., such that at least a portion of the functionality described herein is implemented within the portion of the controller that is externally implemented.

In some embodiments, the controller 30 may communicate with a mobile computing device 60, e.g., through network interface 80, in order to receive the user-selected amount of foodstuff 18 to dispense. In some embodiments, the mobile computing device 60 may contain an application that accepts user input of a user-selected amount of foodstuff 18 to dispense and communicate that user-selected amount to the controller 30, or to multiple controllers 30 of different containers 10, holding different foodstuffs. For example, in some embodiments, the user may enter a recipe into an application of the mobile computing device 60, which may then utilize the amount of various foodstuffs contained within the recipe as the user selection and communicate those user-select amount to the controllers 30 of the containers 10 containing each of required foodstuffs. The mobile device may also, in some embodiments, receive status information from container 10, e.g., amounts dispensed and/or information pertaining to the amount of remaining foodstuff in the container, such that a user may be alerted as to a need to refill the container, and in some instances, to enable a user to order or purchase additional foodstuffs. In some embodiments, for example, reservoirs may be prefilled so that a user may purchase a filled reservoirs for use with dispenser 16 without having to manually fill each reservoir.

In some embodiments, controller 30 may operate under the control of an operating system and may execute or otherwise rely upon various computer software applications, components, programs, objects, modules, data structures, etc. In addition, controller 30 may also incorporate hardware logic to implement some or all of the functionality disclosed herein. Further, in some embodiments, the sequences of operations performed by controller 30 to implement the embodiments disclosed herein may be implemented using program code including one or more instructions that are resident at various times in various memory and storage devices, and that, when read and executed by one or more hardware-based processors, perform the operations embodying desired functionality. Moreover, in some embodiments, such program code may be distributed as a program product in a variety of forms, and that the invention applies equally regardless of the particular type of computer readable media used to actually carry out the distribution, including, for example, non-transitory computer readable storage media. In addition, it will be appreciated that the various operations described herein may be combined, split, reordered, reversed, varied, omitted, parallelized and/or supplemented with other techniques known in the art, and therefore, the invention is not limited to the particular sequences of operations described herein.

In some instances, the container 10 may contain a flow meter 40 that may be disposed in the body 12; the flow meter 40 may either be in addition to, or in place of the pump 20. In embodiments with only a flow meter 40, the flow meter may be configured to measure the amount of the foodstuff 18 dispensed by the dispenser 16. In embodiments with both a pump 20 and a flow meter 40, the flow meter 40 may be capable of measuring the amount of foodstuff 14 conveyed the pump 20, and in some instances the controller 30 may deactivate the pump 20 where the flow meter 40 senses that the user-selected amount of foodstuff 18 has been dispensed. In still other embodiments, the controller 30 may be able to determine the amount of foodstuff 18 present in the reservoir 14 at a given time from one or more readings of the flow meter 40.

In embodiments without a flow meter (i.e. the container only has a pump), the pump 20 may dispense the user-selected amount by running for a predetermined time period knowing a predetermined pump rate. In instances where the contents of the container 10 are known, different flow rates may be used for different materials with differing viscosities to control the dispensation of the foodstuff 18 based on the time period the pump 20 is activated. In some embodiments, this calculation may be performed by a mobile computing device 60 where a user indicated the contents of the container 10, while in other embodiments a user may input this information into the user interface of the container itself, such that an appropriate flow rate may be used to control how long the pump is activated to dispense the user-selected amount of the foodstuff.

In embodiments without a pump (i.e. the container only has a flow meter), a controller-actuated valve may be used to control access to the reservoir; in other words, a valve may open upon receiving a signal from the controller (e.g. that the container 10 is tilted, that user input in the form of a user-selected amount has been received, and/or the like).

In such embodiments, the valve may close once the flow meter senses that the user-selected amount of foodstuff 18 has been dispensed.

As previously mentioned, in some embodiments, the container 10 may additionally include one or more user interfaces disposed on the body 12. These one or more user interfaces may allow a user to select an amount of foodstuff 18 to be dispensed. The one or more user interfaces may be coupled to the controller 30, so that the controller may receive the user-selected amount of the foodstuff to be dispensed. In some embodiments, the user interface may include a button that a user depresses in order to dispense the selected amount of the food stuff. In other embodiments, there may be a display 24 disposed on the body 12 that may transmit information to the controller 30 and/or receive information from the controller 30. For example, such a display 24 may be an LED display that allows a user to select an amount of the foodstuff 18 to dispense; and in some embodiments, the LED display may be a touchscreen display. Furthermore, such an LED display may also provide various alerts to the user, for example that the dispensing is complete, that the reservoir 12 may be in need of refilling (which may be based on a reading from a flow meter 40), or the like. In still other embodiments, the container 10 may also have one or more buttons 22a-f disposed on the body 12 each of which may be coupled to the controller 30.

In some embodiments, a user may depress at least one of the one or more of the buttons 22a-f in order to start/stop the dispensing of the foodstuff. As an illustrative example, a container 10 may have a single button coupled to the controller 30 that, when depressed, activates the pump 20 and allows the foodstuff 18 to be freely dispensed until such a time as the user released the button. In other embodiments, at least one of these one or more buttons 22a-f may be utilized to change the unit of measure (e.g. ounces, cups, tablespoons, teaspoons, or the like) for the user-selected amount of the foodstuff 18 to dispense. For example, such a button may be repeatedly depressed until the desired unit of measure may be reached. In still other embodiments, the container 10 may also include a dial 26 disposed on the body 12 coupled to the controller 30, where a user may rotate the dial 26 to select an amount of the foodstuff 18 to dispense. In some embodiments, the controller 30 may activate the pump 20 to allow free-flow of a foodstuff based on a user input; for example, one of the one or more buttons may be a "free-flow" button that signals the controller 30 to activate the pump 20 to allow free-flow of the foodstuff from the dispenser 16. A container 10 may utilize any combination of user interfaces described, or any combination of other user interfaces known in the art.

In some embodiments, the container 10 may also have a level sensor in the portable body 12 that is coupled with the controller 30 to sense the amount (or level) of the foodstuff 18 that remains in the reservoir 14. In some embodiments, the level sensor may detect a change in weight of the foodstuff 18 and may calculate the amount of foodstuff 18 dispensed based on the change in weight. In other embodiments, the level sensor may detect a change in volume of the foodstuff 18 in the reservoir 14 and may be used to calculate the amount of foodstuff 18 dispensed based on the change in volume. In still other embodiments, the level sensor may include an ultrasonic sensor mounted in the top portion 32 of the container 10 directed to the reservoir 14 in order to determine the level of foodstuff 18 in the resevoir 14. In some instances, this may be desirable so that a user may know when a foodstuff 18 needs refilling or replacing. In some embodiments, the information sensed by the level sensor may be communicated to a user through a user interface or through communication with a mobile computing device 60. For example, a user may receive a communication on a mobile computing device 60 that they almost out of a particular foodstuff.

In some embodiments, the container 10 may also contain a gyroscope 50 coupled to the controller 30, where the gyroscope may sense an angle of orientation of the container 10. In some embodiments, particularly embodiments where the dispenser 14 is location at the top portion 32 of the container 10, where the gyroscope senses that the portable body 12 is upright (i.e., not in a dispensing orientation) the controller 30 may disable the pump 20, or deactivate the dispenser 16 in embodiments without a pump. This may be desirable to create a closed container to keep the foodstuff 18 fresh and to prevent the entry of air, insects, or the like into the container 10 when not in use. In other embodiments where the dispenser 14 is located at the top portion 32 of the container 10, where the gyroscope senses that the portable body 12 is tilted (i.e., in a dispensing orientation) but a user-selected amount has not been received from a user the controller 30 may disable the pump 20, or deactivate the dispenser 16 in embodiments without a pump. This may be desirable to prevent accidental spilling of the foodstuff 18 if the container is knocked-over, or during typically moving and carrying of the container 10. In still other embodiments where the dispenser 14 is located at the top portion 32 of the container 10, where the gyroscope senses that the portable body 12 is tilted (i.e., in a dispensing orientation) and a user-selected amount has been received from a user the controller 30 may activate the pump 20, or dispenser 16 in embodiments without a pump, so that a foodstuff 18 may be dispensed from the reservoir 14. In still yet other embodiments, the controller 30 may activate the pump 20 in response to the titling of the container 10, with or without consideration of a user-selected amount being received by a user. Thus, through the use of the gyroscope, the container may effectively be operated similar to a conventional open pitcher, whereby a user simply tilts the container as with a conventional pouring action to dispense a controlled amount of foodstuff from the container.

Figure 9:
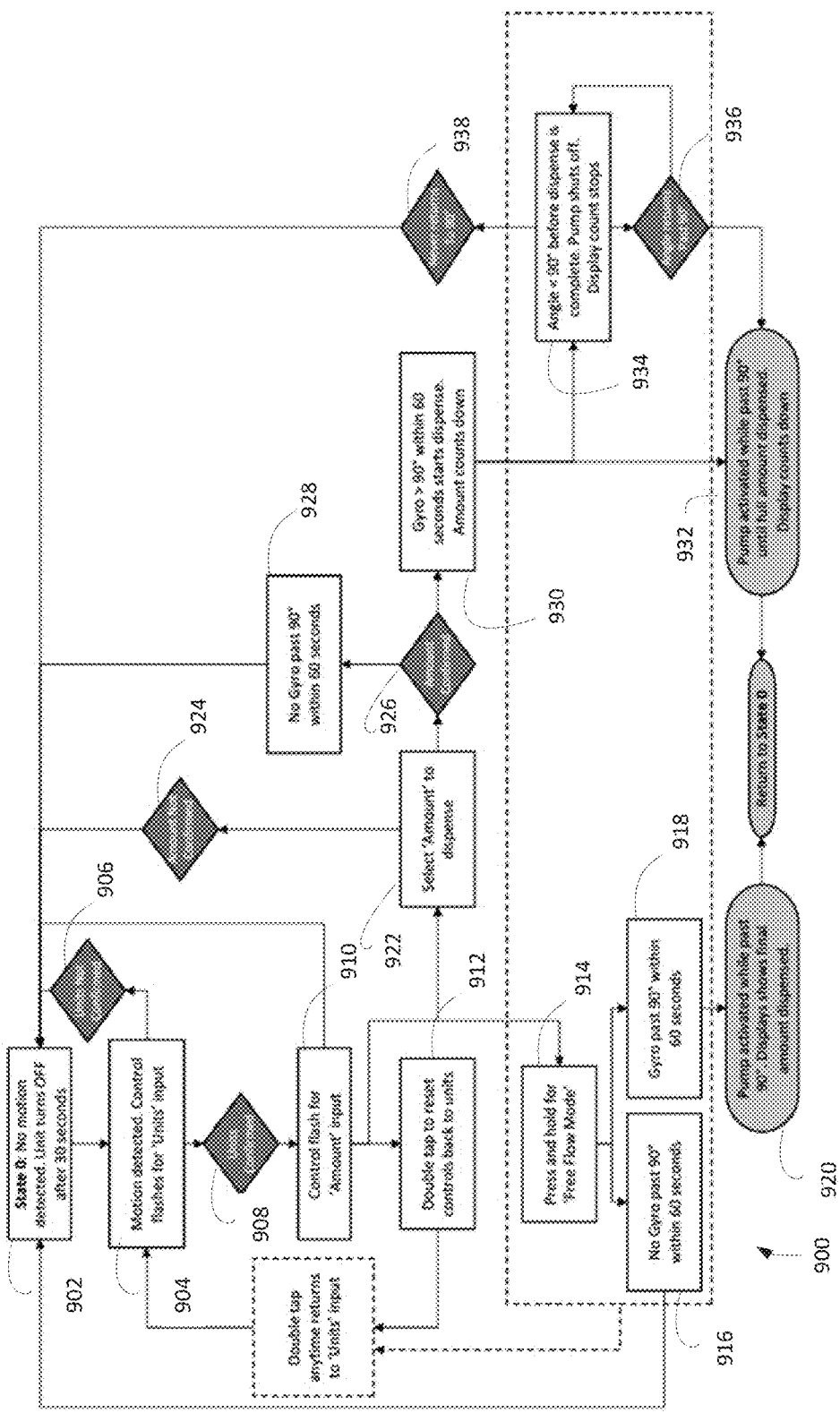
FIG. 9 is an embodiment of an operational flow for the portable foodstuff container of FIG. 1.

Although the container 10 is illustrated in FIGS. 1-4 with the dispenser 16 located proximate a top portion 32 of the container 10, this is not to be understood as limiting. In other embodiments, the dispenser 16 may be located proximate a bottom portion 42 of the container 10, such that foodstuff may be dispensed from the bottom of the container, e.g., similar to a pepper mill, as illustrated in FIG. 9. In still other embodiments, the dispenser 16 may be located anywhere between the top portion 32 and bottom portion 42 of the container 10, or different components of the dispenser may be disposed in different regions of the container (e.g., to dispense foodstuff from the bottom of the dispenser while providing a user interface proximate the top of the container.

Figure 10:
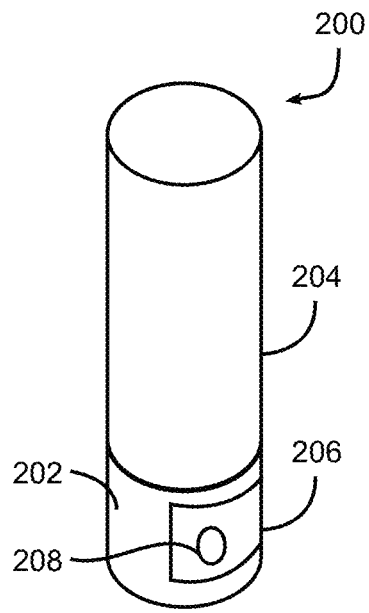
FIG. 10 is a perspective view of a portable foodstuff container consistent with some embodiments of the invention.

As noted above, in some embodiments a portable foodstuff container may dispense from a bottom portion rather than a top portion. FIG. 10, for example, illustrates an example portable foodstuff container 200 having a dispenser 202 and reservoir 204, with the dispenser 202 including a user interface 206 as well as some or all of the other electronic components discussed above, e.g., a pump, flow meter and/or valve for controlling the amount of foodstuff dispensed from the container. In some embodiments, a bottom-dispensing container may be configured to inhibit dispensing whenever the container is not in an upright position (e.g., as sensed by a gyroscope), and further, a user control such as a button 208 may be included to enable a user to initiate a dispensing operation. As such, for a bottom-dispensing container, a dispensing orientation may be substantially upright.

Figure 11:
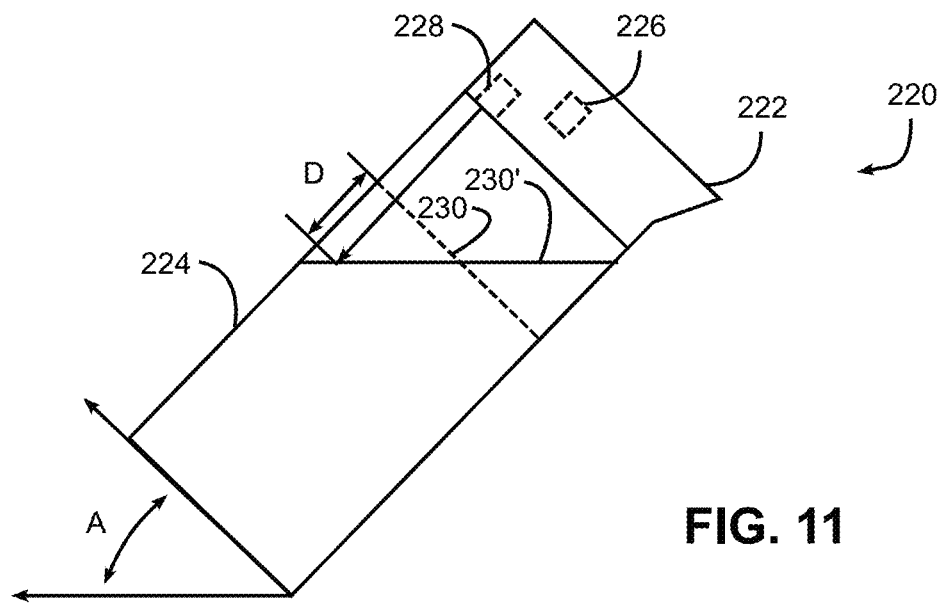
FIG. 11 is a functional vertical section of a portable foodstuff container consistent with some embodiments of the invention.

Now turning to FIG. 11, in some embodiments it may also be desirable to use a level sensor and a gyroscope to sense the relative viscosity of a material in a portable container to provide more accurate dispensing of predetermined amounts of material from the container. FIG. 11, in particular, illustrates a portable container 220 including a dispenser 222 and reservoir 224, along with a gyroscope 226 and level sensor 228. It will be appreciated that the more viscous a material in container 220 is, the greater amount of time it takes to transition to a level state whenever container 220 is tilted. As such, a gyroscope 226 may be used to sense an angle of inclination A of container 220, while a level sensor 228 (e.g., an ultrasonic sensor) may be used to sense the level change of the material during tilting. For example, when container 220 is tilted from an upright orientation where the top surface of the material is illustrated at 230 to the orientation illustrated in FIG. 11, the top surface of the material effectively tilts to the position identified at 230', such that level sensor 228 may be used to sense a distance D between the upright and tilted levels 230, 230' of the material. Moreover, the rate of change over time may be determined from the outputs of gyroscope 226 and level sensor 228 to effectively determine how quickly the surface of the material re-levels, which is related to the viscosity of the material, as more viscous materials will take longer to re-level than less viscous materials.

In some embodiments, therefore, a value representative of viscosity may be determined from the outputs of gyroscope 226 and level sensor 228 over time, and this value may be used to effectively compensate for the viscosity of the material in the container and thereby improve the accuracy of the dispenser when dispensing predetermined amounts (e.g., user-selected amounts) of material. In some embodiments, for example, a value representative of viscosity may be used to scale a dispense time or a dispense rate of a dispenser to compensate for viscosity. The dispense time, for example, may refer to the amount of time that a valve of the dispenser remains open given a predetermined flow rate of the dispenser, and in some embodiments, a baseline flow rate of the dispenser may be determined for a baseline viscosity material, e.g., water, and this baseline flow rate may be scaled to compensate for the viscosity of the actual material being dispensed relative to the viscosity of water. Then, given the scaled flow rate, the baseline (or unscaled) dispense time for dispensing the predetermined amount of material with the baseline viscosity may be scaled to determine a scaled dispense time suitable for dispensing the material, e.g., to extend the dispense time for more viscous materials that flow more slowly through the dispenser.

In other embodiments, e.g., pump-based embodiments where the dispense rate of the dispenser may be varied, the value representative of viscosity may be use to scale a controlled dispense rate of the dispenser to compensate for viscosity, in a similar manner as described above.

It will be appreciated that different embodiments may compensate for viscosity in a number of different manners consistent with the invention, and that the relationships between angle of inclination sensed by a gyroscope, material level sensed by a level sensor, time, and the value representative of viscosity may be implemented in a number of different ways, and may vary in different embodiments based upon the particular dispenser configuration. For example, such relationships may be represented by formulas and/or look-up tables, and may be determined through mathematical calculations based on the configuration of a particular dispenser design and/or through empirical testing of a particular dispenser design. In addition, temperature may also be sensed by a thermocouple or other temperature sensor and used in connection with a gyroscope and level sensor in some embodiments to further compensate for viscosity variations, and in some embodiments, e.g., where the type of material in a container is known, sensed temperature may be used by itself to vary a dispense time and/or dispense rate to account for viscosity variations of a material at different temperatures.

Figure 8:
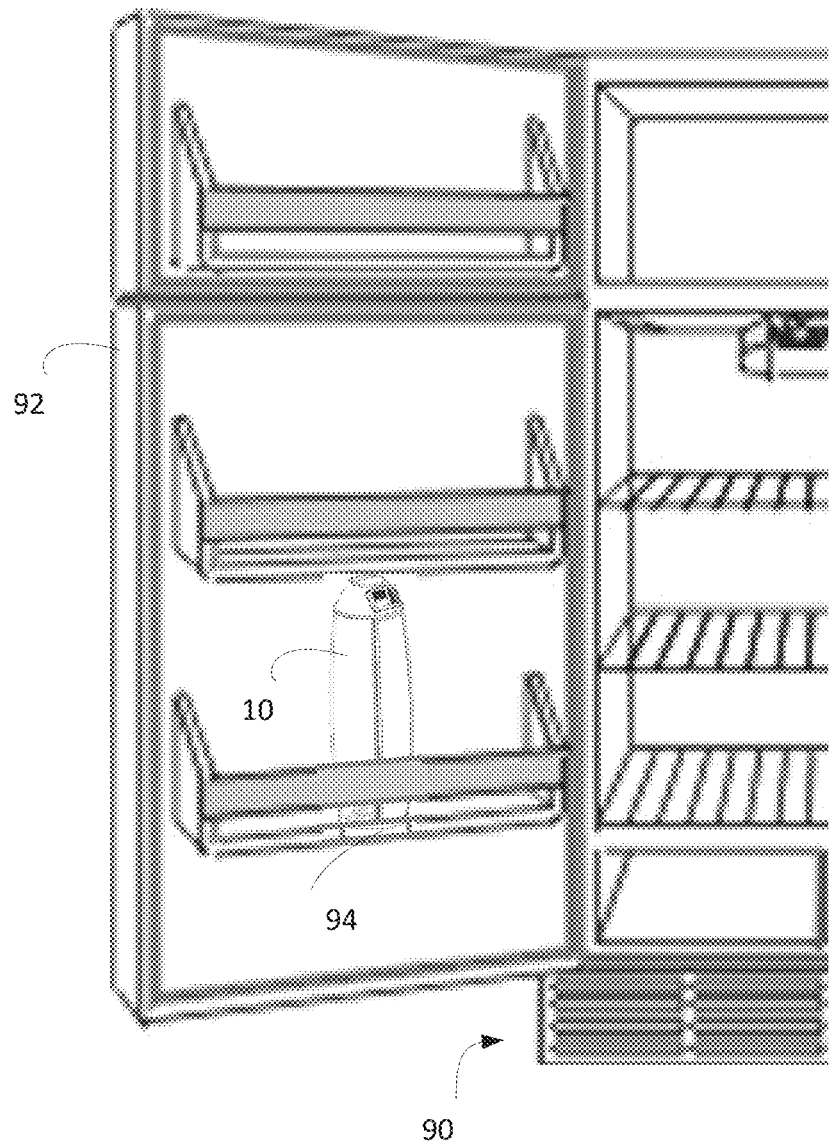
FIG. 8 is a perspective view of a portable foodstuff container consistent with some embodiments of the invention.

In some embodiments, the container 10 may further comprise a battery that provides the necessary power to the pump 20 and the controller 30. In some embodiments, the battery may be replaceable, while in other embodiments the battery may be rechargeable. In rechargeable embodiments, the container 10 may contain one or more battery recharging contacts 44a, 44b. In some embodiments, such battery recharging contacts 44a, 44b may be located at the bottom portion 42 of the container 10 such that the container 10 may be capable of sitting in a charging base (not illustrated). In other embodiments, the battery charging contacts may be located anywhere contact with respective charging portion may be made. In some embodiments, such as illustrated in FIG. 8, the container 10 may be part of a refrigerator system for storage and dispensing of foodstuffs 18 that require cold storage. In some embodiments, the container 10 may be stored in the door 92 of a refrigerator 90, where the door contains a battery charging circuit 94 that charges the container 10 when it is placed in the door 92 of the refrigerator 90. Charging may also be performed wirelessly in some embodiments. However, this should not be understood to be limiting, in other embodiments, the container 10 may be stored in a drawer of the refrigerator 90, or anywhere else inside the refrigerator 90. In still other embodiments, containers may be stored in cabinets, on countertops, or in dedicated holders.

Figure 5:
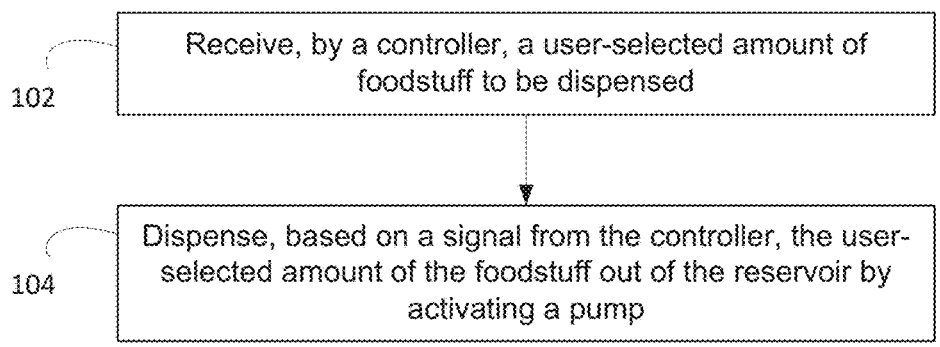
FIG. 5 is a flowchart illustrating an example sequence of operations for dispensing the foodstuff from the portable foodstuff container of FIG. 1.

Conventionally, measurement of foodstuffs for use in cooking requires the use of various measuring devices, such as measuring cups, measuring spoons, and so on. Now turning to FIG. 5, and with continuing reference to FIGS. 1-4, an embodiment of a method 100 for dispensing a portable foodstuff 18 from a container 10 with a portable body 12, that includes a reservoir 14 containing the foodstuff 18 and a dispenser 16 for dispensing the foodstuff 18 contained in the reservoir is illustrated.

In block 102 the controller 30 may receive a user-selected amount of the foodstuff to be dispensed by the dispenser 16. In some embodiments, the user input may come from one or more user interfaces including, but not limited to, one or more dials 26, buttons 22a-f, displays 24, mobile computing devices 60, or the like. In block 104, the user-selected amount of foodstuff 18 may be dispensed from the reservoir by activating the pump 20 based on a signal from the controller 30.

In some embodiments, the method 100 may further include the controller 30 receiving an indication from the gyroscope 50 regarding the orientation of the body 12 of the container 10. In such embodiments, the dispensing of the foodstuff 18 may be performed in response to the determination that the body 12 is titled.

In some embodiments, the method 100 may also include communicating an amount of foodstuff 18 remaining in the reservoir 14 to a mobile computing device 60. In some instances this may be desirable so that the user is aware when they are at risk of running out of the foodstuff. In some embodiments, the mobile computing device 60 may notify the user if the foodstuff 18 is about to be depleted. In other embodiments, when the amount of foodstuff 18 remaining reaches a pre-determined amount (which may vary based on the particular foodstuff) the mobile computing device 60, or an application container thereon, may automatically add the foodstuff to a user's shopping list. In other embodiments, the controller 30 may be in communication with a mobile computing device 60 to receive user input, where the user selects the amount of foodstuff 18 to be dispensed and that amount is communicated to the controller 30. In some embodiments, a user may enter the desired amount of foodstuff into the mobile computing device 60; while in other embodiments, the mobile computing device 60 may comprise an application where a user selects a recipe the information from the recipe regarding the particular foodstuff in the container is utilized as the user-selected amount. In may be desirable, in some embodiments, for various mobile applications of a mobile computing device 60, particularly those applications with recipes or shopping lists, to interface with the container 10.

In other embodiments, the method 100 may also include the controller 30 receiving the amount of foodstuff 18 added to the reservoir 14. Current levels of the amount of foodstuff 18 in the reservoir 14 may be tracked based on the received amount of foodstuff added to the reservoir 14 and the amount of foodstuff 18 dispensed from the reservoir 14 during one or more dispensing cycles. A user may then be notified when the amount of foodstuff 16 currently in the reservoir 16 is running low. In some embodiments, the current level of foodstuff in the reservoir may be stored by the controller and/or may be transmitted to a mobile computing device 60 so that a user may view it at any time.

Figure 6:
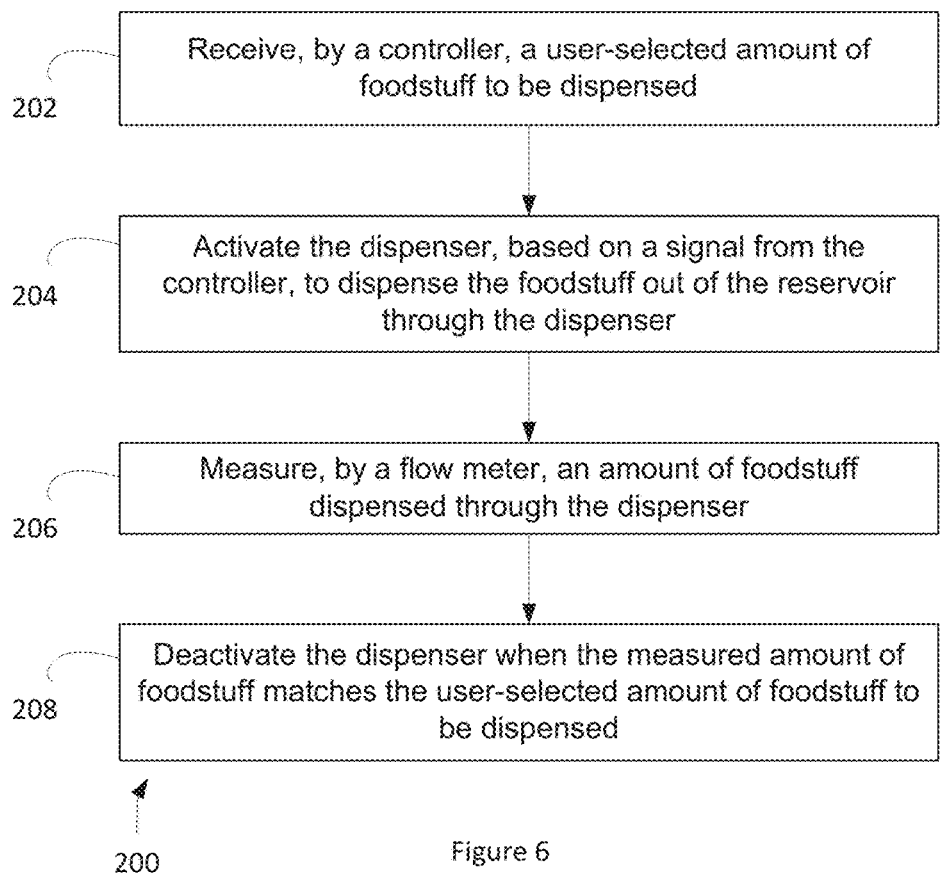
FIG. 6 is a flowchart illustrating another example sequence of operations for dispensing the foodstuff from the portable foodstuff container of FIG. 1.

Now turning to FIG. 6, another embodiment of a method 200 for dispensing a portable foodstuff 18 from a container 10 with a portable body 12, that includes a reservoir 14 containing the foodstuff 18 and a dispenser 16 for dispensing the foodstuff 18 contained in the reservoir is illustrated. In block 202, the controller 30 may receive a user-selected amount of foodstuff 18 to be dispensed. As mentioned previously, the user-selection may come from one or more user interfaces including, but not limited to, one or more dials 26, buttons 22a-f, displays 24, mobile computing devices 60, or the like.

In block 204, the dispenser 16 may be activated based on a signal from the controller 30 to dispense the foodstuff 18 out of the reservoir 14 through the dispenser 16. In block 206, a flow meter 40 may measure the amount of foodstuff 18 dispensed through the dispenser 16. In block 208, the dispenser 16 may be deactivated, when the amount of foodstuff 18 measured by the flow meter 40 matches the amount of foodstuff to be dispensed based on the user-input.

In some embodiments, the method 200 further includes the controller 30 receiving an indication from the gyroscope 50 regarding the orientation of the body 12 of the container 10. In such embodiments, the activation of the dispenser 16 to dispensed foodstuff 18 may be in response to the determination that the body 12 titled.

In some embodiments, the method 200 may also include communicating an amount of foodstuff 18 remaining in the reservoir 14 to a mobile computing device 60. In some instances this may be desirable so that the user is aware when they are at risk of running out of the foodstuff. In some embodiments, the mobile computing device 60 may notify the user if the foodstuff 18 is about to be depleted. In other embodiments, when the amount of foodstuff 18 remaining reaches a pre-determined amount (which may vary based on the particular foodstuff) the mobile computing device 60, or an application container thereon, may automatically add the foodstuff to a user's shopping list. In other embodiments, the controller 30 may be in communication with a mobile computing device 60 to receive user input, where the user selects the amount of foodstuff 18 to be dispensed and that amount is communicated to the controller 30. In some embodiments, a user may enter the desired amount of foodstuff into the mobile computing device 60; while in other embodiments, the mobile computing device 60 may comprise an application where a user selects a recipe the information regarding the particular foodstuff stored in the container from the recipe is utilized as the user-selected amount. In may be desirable, in some embodiments, for various mobile applications of a mobile computing device 60, particularly those applications with recipes or shopping lists, to interface with the container 10.

In other embodiments, the method 200 may also include the controller 30 receiving the amount of foodstuff 18 added to the reservoir 14. Current levels of the amount of foodstuff 18 in the reservoir 14 may be tracked based on the received amount of foodstuff added to the reservoir 14 and the amount of foodstuff 18 dispensed from the reservoir 14 during one or more dispensing cycles. A user may then be notified when the amount of foodstuff 16 currently in the reservoir 16 is running low. In some embodiments, the current level of foodstuff in the reservoir may be stored by the controller and/or may be transmitted to a mobile computing device 60 so that a user may view it at any time.

In some embodiments, the portable foodstuff container 10 may be part of a whole-kitchen system, where a mobile computing device 60 may be utilized to manage a user's kitchen and all foodstuffs therein. As such a user may be able to view the currently levels of all foodstuffs in their kitchen remotely from a mobile computing device 60.

Now turning to FIG. 9, an example embodiment of an operational flow 900 for a portable foodstuff container 10, such as illustrated in FIG. 1 and described herein. In block 902, where no motion is detected, the container 10 (unit) may turn off after 30 seconds. Where motion is detected, in block 904, the container 10 may wait for a unit of measure to be entered. Where no unit of measure is detected, block 906, the container 10 (unit) may automatically turn off after 30 seconds. Where a unit of measure is confirmed, block 908, the container 10 may wait for an amount to be entered, block 910. In some instances, the user may wish to reset the unit back to a unit selection mode, which may be done by double tapping, block 912.

In other instances, a user may desire a free flow of the foodstuff 18 from the container 10. In such instances, the user may press and hold for a "free flow mode", block 914. While in a "free flow mode, in block 916, where the orientation of the container does not surpass 90 degrees, as measured by the gyroscope 50, within 60 seconds, block 916, the container 10 may turn off, block 902. However, where the orientation of the container surpasses 90 degrees, as measured by a gyroscope, within 60 seconds, block 918, the pump 20 may be activated while the container 10 is past 90 degrees, block 920. The display may also show a user how much foodstuff 18 has been dispensed in the "free flow mode".

In still other instances, a user may select an amount to dispense, block 922. Where the amount is not confirmed by the user, block 924, the container 10 (unit) may automatically turn off after 30 seconds, block 902. Where the amount is confirmed, block 926, the orientation of the container 10, by a gyroscope may be examined. Where the orientation of the container does not surpass 90 degrees, as measured by the gyroscope 50, within 60 seconds, block 928, the container 10 may turn off, block 902. However, where the orientation of the container surpassed 90 degrees, as measured by a gyroscope, within 60 seconds, the foodstuff 18 may be dispensed while the amount selected by the user counts down, block 930. The pump may remain activated while the container 10 surpasses 90 degrees, as measured by a gyroscope 50, until the user selected amount is fully dispensed, block 932. Where the angle of the container 10, as measured by the gyroscope 50, is less than 90 degrees before the dispensing is complete, the pump 20 may shut off and the display may stop counting, block 934. If the angle returns to greater than 90 degrees, block 936, then the pump may remain active until the user-selected amount is fully dispensed, block 932. Where the container 10 never returns to an orientation of greater than 90 degrees, as measured by the gyroscope 50, block 938, the container 10 shuts off, block 902.

It is to be understood that the operational flow illustrated in FIG. 9 and described herein is merely one example of a possible operational flow, and is not to be understood as limiting.

Various additional modifications may be made to the illustrated embodiments consistent with the invention. Therefore, the invention lies in the claims hereinafter appended.

What is claimed is:

1. A portable foodstuff container, comprising:
    a portable body including a reservoir configured to contain a foodstuff and a dispenser configured to dispense the foodstuff contained in the reservoir;
    a gyroscope coupled to body and configured to sense an orientation of the body;
    a pump disposed within the body and configured to convey the foodstuff from the reservoir to the dispenser when activated to dispense the foodstuff through the dispenser; and
    a controller disposed in the body and coupled to the gyroscope and the pump, wherein the controller is configured to determine whether the body is in a dispensing orientation using the gyroscope and activate the pump while the body is determined to be in the dispensing orientation to dispense a user-selected amount of foodstuff from the dispenser, and wherein the controller is further configured to deactivate the pump prior to dispensing all of the user-selected amount of foodstuff from the dispenser in response to determining that the body is no longer in the dispensing orientation.

2. The container of claim 1, wherein the container further comprises a flow meter disposed in the body and configured to measure an amount of foodstuff conveyed by the pump, and wherein the controller is configured to deactivate the pump upon sensing with the flow meter that the user-selected amount has been dispensed.

3. The container of claim 2, wherein the controller is configured to determine an amount of foodstuff present in the reservoir based on one or more readings from the flow meter.

4. The container of claim 1, further comprising a user interface disposed on the body and coupled to the controller to receive user input selecting the user-selected amount, and wherein the user interface includes a control that a user selects to dispense the user-selected amount of foodstuff.

5. The container of claim 1, further comprising a dial disposed on the body and coupled to the controller to receive user input selecting the user-selected amount by rotation.

6. The container of claim 1, further comprising a control disposed on the body and coupled to the controller to change a unit of measure of the user-selected amount.

7. The container of claim 1, further comprising a level sensor in the body and coupled to the controller to sense an amount of the foodstuff remaining in the reservoir.

8. The container of claim 1, further comprising a battery in the body configured to provide power to the pump and the controller.

9. The container of claim 8, wherein the battery is rechargeable.

10. The container of claim 1, wherein the pump is disposed in a channel between the reservoir and the dispenser.

11. The container of claim 1, wherein the dispenser is located proximate a bottom portion of the body.

12. The container of claim 1, wherein the dispenser is located proximate a top portion of the body.

13. The container of claim 1, wherein the controller is configured to communicate with a mobile computing device to receive the user-selected amount.

14. The container of claim 13, wherein the mobile computing device further comprises an application configured to accept user input of the user-selected amount and communicate the user-selected amount to the controller.

15. The container of claim 1, wherein the controller is further configured to activate the pump to free flow based on user input.

16. The container of claim 1, wherein the controller is further configured to activate the pump to automatically start dispensing the user-selected amount in response to tilting of the body from a non-dispensing orientation to the dispensing orientation.

17. The container of claim 1, wherein the container is configured for storage in a refrigerator and includes a battery charging circuit configured to charge a battery of the container when the container is stored in the refrigerator.

18. The container of claim 1, wherein the controller is configured to activate the pump to dispense the user-selected amount of foodstuff from the dispenser additionally in response to selection of a user control while the body is determined to be in a dispensing orientation.

19. The container of claim 1, wherein the controller is further configured to, after deactivating the pump prior to dispensing all of the user-selected amount of foodstuff from the dispenser, reactivate the pump to complete dispensing of the user-selected amount of foodstuff from the dispenser in response to determining that the body is again in the dispensing orientation.

20. The container of claim 1, wherein the controller is further configured to, in response to an absence of user input, disable activation of the pump when the body is in the dispensing orientation.

21. The container of claim 1, wherein the controller is further configured to, in response to the user-selected amount not being received, disable activation of the pump when the body is in the dispensing orientation.

22. The container of claim 1, further comprising a level sensor coupled to the body, wherein the controller is further configured to:
    sense tilting of the portable container with the gyroscope;
    sense a level change of the material in the portable container using the level sensor during tilting of the portable container;
    determine a value representative of a viscosity of the material based upon the sensed tilting and sensed level change; and control the amount of material dispensed from the portable container using the determined value.

23. The container of claim 1, wherein the controller is configured to determine that the body is in a dispensing orientation in response to determining that an orientation of the body surpasses 90 degrees.

24. A portable foodstuff container, comprising:
a portable body including a reservoir configured to contain a foodstuff and a dispenser configured to selectively dispense the foodstuff contained in the reservoir;
a gyroscope coupled to the body and configured to sense an orientation of the body;
a flow meter disposed in the body and configured to measure an amount of foodstuff dispensed by the dispenser; and
a controller coupled to the gyroscope, the flow meter and the dispenser, wherein the controller is configured to determine whether the body is in a dispensing orientation using the gyroscope and control the dispenser while the body is determined to be in the dispensing orientation to dispense a user-selected amount of foodstuff in response to the amount of foodstuff sensed by the flow meter, and wherein the controller is further configured to control the dispenser to discontinue dispensing prior to dispensing all of the user-selected amount of foodstuff from the dispenser in response to determining that the body is no longer in the dispensing orientation.

25. The container of claim 24, wherein the controller is further configured to control the dispenser to automatically start dispensing the user-selected amount in response to tilting of the body from a non-dispensing orientation to the dispensing orientation.

26. The container of claim 24, wherein the controller is configured to control the dispenser to dispense the user-selected amount of foodstuff additionally in response to selection of a user control while the body is determined to be in a dispensing orientation.

27. The container of claim 24, wherein the controller is further configured to, after discontinuing dispensing prior to dispensing all of the user-selected amount of foodstuff, control the dispenser to complete dispensing of the user-selected amount of foodstuff in response to determining that the body is again in the dispensing orientation.

* * * * *